(12) United States Patent
Nolen et al.

(10) Patent No.: US 6,866,858 B2
(45) Date of Patent: Mar. 15, 2005

(54) METHOD AND COMPOSITIONS FOR ATTRACTING MOSQUITOES

(75) Inventors: Jim A. Nolen, W. Greenwich, RI (US); Robert H. Bedoukian, West Redding, CT (US); Daniel L. Kline, Gainesville, FL (US)

(73) Assignees: BioSensory, Inc., Willimantic, CT (US); Bedoukian Research, Inc., Danbury, CT (US); The United States of America, as represented by the Secretary of Agriculture, Washington, DC (US)

( * ) Notice: Subject to any disclaimer, the term of this patent is extended or adjusted under 35 U.S.C. 154(b) by 493 days.

(21) Appl. No.: 09/752,704

(22) Filed: Dec. 28, 2000

(65) Prior Publication Data

US 2002/0127258 A1 Sep. 12, 2002

(51) Int. Cl.$^7$ ............... A01N 25/32; A01N 59/04; A01N 31/02
(52) U.S. Cl. ............ 424/406; 424/405; 424/700; 424/84; 424/44; 514/739
(58) Field of Search ............ 424/84, 405, 406, 424/700, 44; 514/739

(56) References Cited

U.S. PATENT DOCUMENTS

| | | | |
|---|---|---|---|
| 5,205,064 A | 4/1993 | Nolen | 43/112 |
| 5,669,176 A | 9/1997 | Miller | 43/139 |
| 5,721,274 A * | 2/1998 | Vander Meer et al. | 514/532 |
| 5,799,436 A | 9/1998 | Nolen et al. | 43/112 |
| 5,813,166 A | 9/1998 | Wigton et al. | 43/107 |
| 6,055,766 A | 5/2000 | Nolen et al. | 43/112 |
| 6,267,953 B1 * | 7/2001 | Bernier | 424/84 |
| 6,362,235 B1 * | 3/2002 | Nolen et al. | 514/739 |

OTHER PUBLICATIONS

Antennal Response—1–octen–3–01 Saini et al.: Physiol. Ent. (14) 85–90 1989.*

Saini et al Physiol. Entomol. (4(1) 85–90, 1989.*

* cited by examiner

*Primary Examiner*—Neil S. Levy
(74) *Attorney, Agent, or Firm*—Ohlandt, Greeley, Ruggiero & Perle, LLP; George W. Rauchfuss, Jr.

(57) ABSTRACT

1-Alkyn-3-ol compounds of the formula:

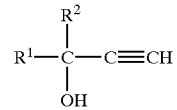

where $R^1$ is a saturated aliphatic hydrocarbon group containing from 1 to about 12 carbon atoms, and $R^2$ is a hydrogen, are effective attractants for mosquitoes.

18 Claims, No Drawings

METHOD AND COMPOSITIONS FOR ATTRACTING MOSQUITOES

FIELD OF THE INVENTION

This invention relates to a method and compositions for attracting mosquitoes so that they may be captured and/or killed. More particularly, the invention relates to the use of certain compounds in compositions and apparatus to more effectively attract mosquitoes.

BACKGROUND

Compounds, compositions and formulations for protecting human beings from being bitten by mosquitoes are known in the art. Generally, these compounds, compositions and formulations are based on their ability to persist on the skin of the person upon topical or surface application for a time sufficient to repel mosquitoes, or are based on their ability to attract mosquitoes so that the mosquitoes may be captured and/or killed so that they are unable to bite human beings or other animals. However, despite the various attempts to improve the attractant activity of the known mosquito attractants, these attempts have generally not been successful, as almost anyone who has used such mosquito attractants can attest.

A device for attracting and destroying mosquitoes is disclosed in U.S. Pat. No. 5, 799,436 of James Nolen et al. The attractant used in the device disclosed in this patent is octenol (1-octen-3-ol) used in combination with heat and carbon dioxide.

The art has been searching for new and more effective attractants for mosquitoes. However, the search for more effective mosquito attractants has not generally been met with much success since most mosquito attractants have been found only to possess a limited degree of attractance activity and are generally not particularly effective. There is, therefore, a need for more effective means to attract mosquitoes in order to prevent the mosquitoes from locating and biting humans and other targets such as livestock. Moreover, this need has recently become more acute and urgent because mosquitoes have been discovered to be carriers of significant diseases that can be passed on to a target by the mosquitoes biting the target. A further need is to be able to reduce the use of environmentally unfriendly pesticides.

SUMMARY OF THE INVENTION

The inventors have discovered compounds useful in compositions and formulations and in methods and apparatus for attracting mosquitoes. When an effective amount of the attractant compound(s) is/are deployed in a three dimensional atmospheric space the compound(s) more effectively attract mosquitoes so they can be captured and/or killed.

According to this invention, compounds selected from the group consisting of 1-alkyn-3-ols of the formula:

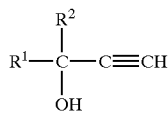

wherein $R^1$ is a saturated aliphatic hydrocarbon group containing from 1 to about 12 carbon atoms, and $R^2$ is hydrogen, preferably hydrogen are especially effective as attractants for mosquitoes. Preferably, $R^1$ is $C_5H_{11}$.

The attractant compound can be dispensed into three dimensional atmospheric space by any suitable means sufficient to provide an attracting effective amount of the attractant compound(s). Such dispensing means includes, for example, evaporation, atomization and ionic dispersion of the attractant compound from any suitable composition or formulation and apparatus. Such composition or formulation will generally comprise a base vehicle containing at least one of the attractant compounds.

DETAILED SUMMARY OF THE INVENTION

The inventors have discovered that when an effective amount of at least one attractant compound selected from the group consisting of 1-alkyn-3-ols of the formula:

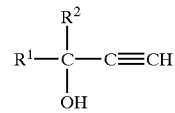

wherein $R^1$ is a saturated aliphatic hydrocarbon group containing from 1 to about 12 carbon atoms, and $R^2$ is hydrogen, is dispensed into the atmosphere of a three dimensional environmental space, mosquitoes are attracted to the attractant compound and are susceptible to being captured and/or killed.

Any suitable 1-alkyn-3-ols of the formula:

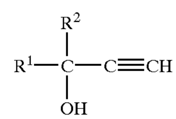

wherein $R^1$ and $R^2$ are as defined hereinbefore may be employed in the method, compositions and apparatus of this invention. Preferred suitable inhibiting compounds are, for example, 1-octyn-3-ol, 1-decyn-3-ol, 1-heptyn-3-ol, 1-butyn-3-ol and 1-tetradecyn-3-ol, and preferably 1-octyn-3-ol. Depending on the particular mosquito species, a particular 1-alkyn-3-ol may be more effective and be preferred for that species of mosquito. The attractant compounds may be utilized singly or as mixtures of two or more of such compounds. Moreover, the attractant compounds of this invention can be utilized in combination with other known mosquito attractants, such as for example, in combination with carbon dioxide and/or heat.

The 1-alkyn-3-ols of this invention can be prepared by the reaction of an appropriate aldehyde with sodium acetylide according the following reaction where $R^1$ and $R^2$ are as defined herein before.

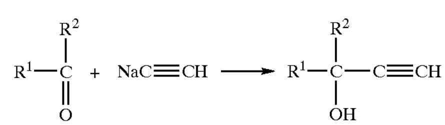

For example, 1-octyn-3-ol was prepared by charging 220 g of 18% sodium acetylide in xylene to a flask containing 100 g tetrahydrofuran and 16 g dimethylformamide. The reaction mixture was stirred and heated to 30° C. Then 80 g of n-hexanal dissolved in 40 g tetrahydrofuran was fed to the reaction mixture while permitting the reaction temperature to rise to about 40° C. during the feeding. The reaction mixture was stirred for about 30 minutes after completion of the feed. The reaction mixture was then washed twice with water and distilled to provide 1-octyn-3-ol.

Any suitable attracting effective amount of the attractant compound(s) may be employed. Such attracting effective amounts will generally range from about 0.01 mg/hr to about 10 mg/hr, preferably from about 0.04 mg/hr to about 3.5 mg/hr.

The attractant compound(s) of this invention may be employed in any formulation suitable for dispensing attractant effective amounts of the compounds. The compounds will generally be employed in formulations comprising a suitable vehicle or carrier containing the attractant compounds. For example, the attractant compound can be formulated in a specially formulated waxy medium or vehicle engineered to release desired amounts of vaporous attractant compound at ambient temperatures, such as those waxy mediums or vehicles available from Koster Keunen of Watertown, Conn. An example of such a waxy medium available from Koster Keunen is known as Insect Repellent Wax Bar No. 9, which is a blend of waxes having the following general composition: fatty acids ranging in carbon chain length of from $C_{16}$ to $C_{22}$, fatty alcohols ranging in carbon chain length of from $C_{16}$ to $C_{22}$, paraffinic hydrocarbons ranging in carbon chain length of from $C_{19}$ to $C_{47}$, branched hydrocarbons ranging in carbon chain length of from $C_{23}$ to $C_{69}$, beeswax and other natural waxes such as candelilla and carnauba. The wax mixture will generally be formulated with concentrations of the attractant compounds of this invention ranging from about 20% to 60% and the formulation has a congealing point which may vary from about 75° C. to about 45° C. Alternatively, the inhibiting compound can be formulated in a porous medium or vehicle suitable for releasing effective amounts of the attractant compound. As an example of such porous medium or vehicle is a polyester membrane material having micropores encasing a block of inhibiting compound saturated fibers that gradually releases the inhibiting compound so that it permeates the microporous membrane and is released to the environment. Such porous membrane known as World of Fragrance™ cups is available from Waterbury Companies, Inc. of Waterbury, Conn.

The formulations can be placed in any suitable container or device for dispensing the attractant compound and attracting or trapping mosquitoes. For example, the formulations can be placed in a suitable device so that one can obtain, for example, evaporation of the attractant compound from a porous medium or wax-like medium containing the attractant compound positioned within the dispensing device. As examples of such devices, there can be mentioned the devices disclosed in U.S. Pat. Nos. 5,205,064, 5,799,436 and 6,055,706 of BioSensory Insect Control Corporation and James Nolen 7 Company, each of said patents being incorporated herein by reference thereto. The formulations can also be placed in jar traps such as those which dispense carbon dioxide as an attractant. The formulations can also be placed in "bug zapping" devices for electrocuting the mosquitoes attracted to the device containing the attractant-containing formulation.

Another suitable means of dispensing the attractant compound is by atomization and/or ionic dispersion of the compound as suitable-sized, positively-charged droplets from a suitable atomization or ionic dispersing apparatus, such as the Ionic Wind™ device, available from Brandenburg, Ltd. of Brierery Hill, United Kingdom used in connection with any suitable mosquito trapping device or apparatus.

The attractant compounds of this invention are effective for mosquitoes, including but not limited to, such as for example, *Aedes taeniorhyncus* (Black Salt Marsh mosquito), *Culex nigripalpus, Aedes aegypti, Aedes albopictus* (Asian Tiger mosquito), *Culex pipiens* (common house mosquito), *Culex quinquefasciatus, Anopheles gambiae* and the like.

The use of the attractant compounds of this invention and their greatly increased attractant property as compared to prior art attractants is illustrated by the following non-limited example.

EXAMPLE

The following tests were conducted by the United States Department of Agriculture in Florida in a large outdoor screened cage of a size of approximately 30 ft.×60 ft.×20 ft. (9.144×18.288×6.096 meters). Into approximately the center of the base of the cage was placed a CFG 6 Collection Jar of American Biophysics providing 500 cc/min $CO_2$. Also placed in the CFG-6 Jar was a fibrous absorbent into which had been absorbed 250 µL of the test attractant compound. There were then introduced into the cage, from the periphery thereof, 1000 *Aedes taeniorhyncus* mosquitoes. After a period of several hours the collection jar was examined to determine the number of mosquitoes captured. As controls, similar tests were run with the CF 6 Collection jar without any attractant compound, i.e. with only $CO_2$. Three replicate tests were run with each test attractant compound. The compound 1-octyn-3-ol was employed as the attractant compound of this invention and 1-octenol as an example of a prior art attractant. The results of the test were as follows.

| Test No: | Mosquitoes captured |
|---|---|
| Test with 1-octyn-3-ol | |
| 1 | 779 |
| 2 | 599 |
| 3 | 826 |
| Total captured: | 2204 |
| Average captured: 735 | |
| Average captured in controls: 334 | |
| Average increase in capture over control: 401 | |
| Comparative test with 1-octen-3-ol | |
| C1 | 624 |
| C2 | 560 |
| C3 | 520 |
| Total captured: | 1704 |
| Average captured: 568 | |
| Average captured in controls: 334 | |
| Average increase in capture over control: 234 | |

The 1-octyn-3-ol attractant compound of this invention captured over 71% more mosquitoes than the prior art 1-octen-3-ol attractant illustrating the unexpectedly greater attractant property of the alkyn-ols of this invention compared to the alken-ols of the prior art.

With the foregoing description of the invention, those skilled in the art will appreciate that modifications may be made to the invention without departing from the spirit thereof. Therefore, it is not intended that the scope of the invention be limited to the specific embodiments illustrated and described.

We claim:

1. A method of attracting mosquitoes within a three-dimensional space comprising releasing within the three-dimensional space a mosquito attracting effective amount of carbon dioxide and at least one 1-alkyn-3-ol of the formula:

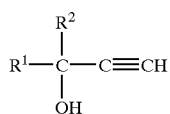

wherein $R^1$ is a saturated aliphatic hydrocarbon group containing from 1 to about 12 carbon atoms, and $R^2$ is hydrogen and wherein the amount of the at least one 1-alkyn-3-ol released is from about 0.01 mg/hr to about 10 mg/hr.

2. A method of claim 1 wherein the at least one 1-alkyn-3-ol comprises 1-octyn-3-ol.

3. A method of attracting mosquitoes within a three-dimensional space comprising releasing within the three-dimensional space a mosquito attracting effective amount of at least one 1-alkyn-3-ol of the formula:

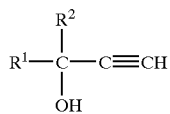

wherein $R^1$ is a saturated aliphatic hydrocarbon group containing from 1 to about 12 carbon atoms, and $R^2$ is hydrogen.

4. The method of claim 3 wherein $R^1$ is $C_5H_{11}$.

5. The method of claim 3 wherein the attracting effective amount ranges from about 0.01 mg/hr to about 10 mg/hr.

6. The method of claim 3 wherein the attracting effective amount ranges from about 0.04 mg/hr to about 3.5 mg/hr.

7. The method of claim 4 wherein the attracting effective amount ranges from about 0.01 mg/hr to about 10 mg/hr.

8. The method of claim 4 wherein the attracting effective amount ranges from about 0.04 mg/hr to about 3.5 mg/hr.

9. The method of claim 3 wherein the releasing comprises evaporation, atomization or ionic dispersion.

10. The method of claim 4 wherein the releasing comprises evaporation, atomization or ionic dispersion.

11. The method of claim 6 wherein the releasing comprises evaporation, atomization or ionic dispersion.

12. The method of claim 8 wherein the releasing comprises evaporation, atomization or ionic dispersion.

13. The method of claim 4 wherein carbon dioxide is released concurrently with the at least one 1-alkyn-3-ol.

14. The method of claim 6 wherein carbon dioxide is released concurrently with the at least one 1-alkyn-3-ol.

15. The method of claim 8 wherein carbon dioxide is released concurrently with the at least one 1-alkyn-3-ol.

16. The method of claim 11 wherein carbon dioxide is released concurrently with the at least one 1-alkyn-3-ol.

17. The method of claim 12 wherein carbon dioxide is released concurrently with the at least one 1-alkyn-3-ol.

18. A method of claim 2 wherein the releasing of the 1-octyn-3-ol comprises evaporation, atomization or ionic dispersion.

* * * * *